United States Patent [19]

Asato et al.

[11] 4,026,903
[45] May 31, 1977

[54] SUBSTITUTED 5-NITROIMIDAZOLES

[75] Inventors: Goro Asato, Titusville; Gerald Berkelhammer, Princeton; William Henry Gastrock, Hightstown, all of N.J.

[73] Assignee: American Cyanamid Company, Stamford, Conn.

[22] Filed: Nov. 18, 1975

[21] Appl. No.: 632,941

Related U.S. Application Data

[60] Division of Ser. No. 409,505, Oct. 25, 1973, Pat. No. 3,940,411, which is a division of Ser. No. 202,568, Nov. 26, 1971, Pat. No. 3,790,589, which is a division of Ser. No. 863,378, Oct. 2, 1969, Pat. No. 3,649,638, which is a continuation-in-part of Ser. No. 766,984, Oct. 11, 1968, abandoned.

[52] U.S. Cl. .............................................. 260/309

[51] Int. Cl.$^2$ ...................................... C07D 233/95
[58] Field of Search ........................ 260/309, 244 R

[56] References Cited

UNITED STATES PATENTS

| | | | |
|---|---|---|---|
| 3,341,549 | 9/1967 | Henry ................................ | 260/309 |
| 3,515,728 | 6/1970 | Henry et al. ....................... | 260/309 |
| 3,565,892 | 2/1971 | Asato et al. ....................... | 260/309 |
| 3,649,638 | 3/1972 | Asato et al. ....................... | 260/309 |
| 3,940,411 | 2/1975 | Asato et al. ................... | 260/308 R |

*Primary Examiner*—Natalie Trousoe
*Attorney, Agent, or Firm*—Charles F. Costello, Jr.

[57] ABSTRACT

This invention relates to new chemical compounds of the class 1-substituted-5-nitro-2-substituted imidazoles and methods for the preparation thereof. These compounds are useful for their anti-microbial activity.

5 Claims, No Drawings

SUBSTITUTED 5-NITROIMIDAZOLES

This is a division, of application Ser. No. 409,505, filed Oct. 25, 1973, now U.S. Pat. No. 3,940,411 which is a division of application Ser. No. 202,568, filed Nov. 26, 1971, now U.S. Pat. No. 3,790,589, which was a division of application Ser. No. 863,378, filed Oct. 2, 1969, Oct. 2, 1969, now U.S. Pat. No. 3,649,638 which was a continuation-in-part of application Ser. No. 766,984, filed Oct. 11, 1968, now abandoned.

SUMMARY OF THE INVENTION

The present invention relates to new chemical compounds of the formulae:

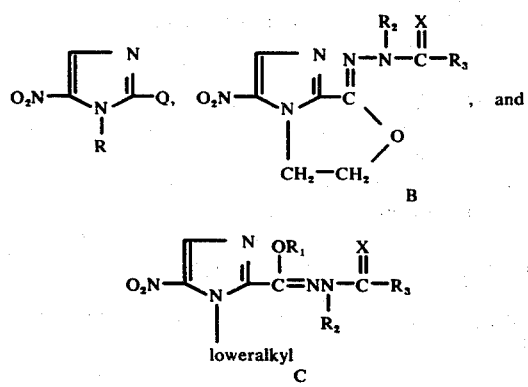

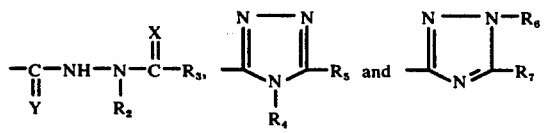

wherein Q is a member selected from the group consisting of

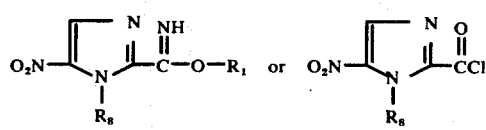

wherein R is loweralkyl or hydroxyloweralkyl; $R_1$ is loweralkyl; $R_2$ and $R_4$ are hydrogen or loweralkyl; $R_3$ is lower alkyl, amino, monoloweralkylamino, or diloweralkylamino with the proviso that in formulae B and C $R_3$ cannot be loweralkyl; $R_5$ is loweralkyl, hydroxy, amino, monoloweralkylamino, or diloweralkylamino, $R_6$ is lower alkyl; $R_7$ is hydroxy or amino; X is NH, oxygen, or sulfur and Y is NH or oxygen. The term lower alkyl is intended to include those containing from 1 to 4 carbon atoms. When an amino, monoloweralkylamino, or hydroxy group is attached to the triazole ring the compound may exist, at least in part, in the tautomeric imino or keto forms.

The invention also relates to methods for th preparation of these compounds, one of which involves the reaction of an imidazolecarboximidate or an acid chloride of the formulae:

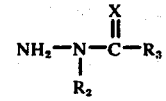

wherein $R_1$ and $R_8$ are loweralkyl or of

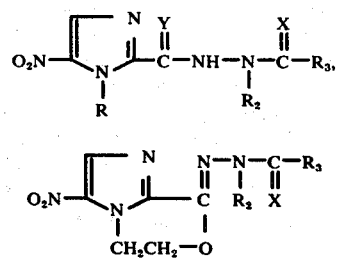

with a semicarbazide, thiosemicarbazide, acylhydrazide or aminoguanidine of the formula:

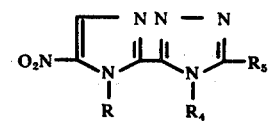

wherein $R_2$, $R_3$ and X are as defined above, to obtain an imidazolecarboximidoyl or imodazolecarbonyl compound or a nitrogenous derivative of an alkyl imidazolecarboxylate of the formulae:

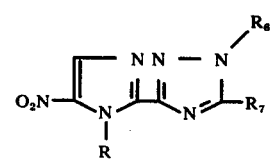

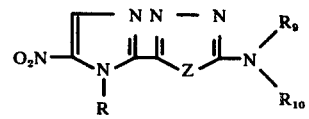

wherein R, $R_1$, $R_2$, $R_3$, X and Y are as defined above, and cyclizing said compound by subjecting the same to heat treatment, acid treatment or treatment with a condensing agent to yield a cyclized product of the formula selected from the group consisting of wherein Z is sulfur or oxygen and R, $R_4$, $R_5$, $R_6$, $R_7$ are as defined above and $R_9$ and $R_{10}$ are hydrogen or lower alkyl.

PREFERRED EMBODIMENT

In accordance with the preferred method of the present invention a 2-cyano-1-loweralkyl-5-nitroimidazole is admixed with an absolute alcohol such as methanol, ethanol or the like and heated in the presence of a strong base such as an alkali metal alkoxide, including potassium t-butoxide and sodium ethoxide, to yield a 1-loweralkyl-5-nitroimidazole-2-carboximidate. The carboximidate is then converted to the imidazolecarboximidoyl acylhydrazide, amidinohydrazine, semicarbazide or thiosemicarbazide by reaction with an acylhydrazine, aminoguanidine, semicarbazide or thiosemicarbazide, respectively. This reaction is preferably carried out in the presence of a solvent inert to the reaction such as a loweralkanol, glacial acetic acid or aqueous alcoholic mixtures and at a temperature between about 20° C. and 100° C. although somewhat higher or lower temperatures may be employed. In the case of reaction of the carboximidate with thiosemicarbazide or substituted thiosemicarbazides, it is found that acid catalysis is necessary, the reaction preferably being carried out in glacial acetic acid or in an alcoholic solvent to which 1 to 50% by volume of acetic acid or catalytic amounts of mineral acids are added. When mineral acids are used, it is frequently found that mixtures of imidazolecarboximidoyl thiosemicarbazides with alkyl 1-substituted-5-nitro-2-imidazolecarboxylate thiosemicarbazones are formed. The latter compounds are obtained as important components of the mixtures, and may be isolated, when 1 or more equivalents of mineral acid, rather than a catalytic amount, is used.

Cyclization of the thus prepared imidazolecarboximidoyl acylhydrazines, amidinohydrazines, or semicarbazides then yields the triazol-3-yl-5-nitroimidazoles. Cyclization of the imidazolecarboximidoylthiosemicarbazides or the imidazolecarboxylate thiosemicarbazones gives 2-(2-amino-1,3,4-thiadiazol-5-yl)-5-nitroimidazoles. These reactions, in the case of the triazol-3-yl-5-nitroimidazoles, are generally most favorably carried out by heating, preferably refluxing, in the presence of an organic solvent such as nitrobenzene, dimethylformamide or glacial acetic acid. In the case of the thiadiazol-5-yl-5-nitroimidazoles acid catalysis is generally most advantageously employed. Acidic reagents such as aqueous, methanolic, or ethanolic sulfuric or hydrochloric acids are preferred, however, other acids such as phosphoric, nitric, hydrobromic trifluoroacetic and aliphatic or aromatic sulfonic acids may also be used. p-Toluene sulfonic acid and methylsulfonic acids are typical of these latter acid groups. In practice it is also found that the acid catalysts may be conducted in systems free of solvent or in the presence of solvents other than water or lower alcohols. Furthermore, it has been found that these reactions are generally most advantageous carried out at temperatures between 0° C. and 150° C. and preferably 50° C. and 100° C.

Graphically, such reactions may be illustrated as follows:

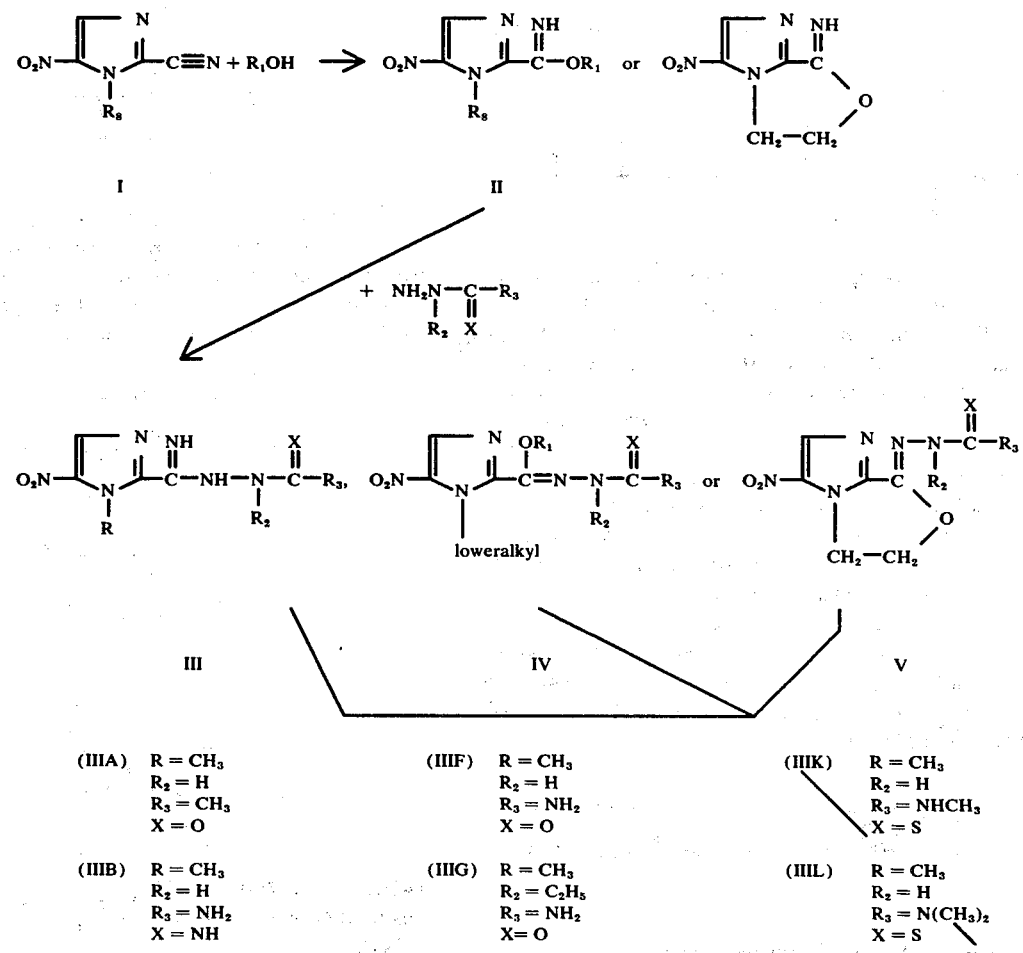

| (IIIA) | R = CH₃<br>R₂ = H<br>R₃ = CH₃<br>X = O | (IIIF) | R = CH₃<br>R₂ = H<br>R₃ = NH₂<br>X = O | (IIIK) | R = CH₃<br>R₂ = H<br>R₃ = NHCH₃<br>X = S |
| --- | --- | --- | --- | --- | --- |
| (IIIB) | R = CH₃<br>R₂ = H<br>R₃ = NH₂<br>X = NH | (IIIG) | R = CH₃<br>R₂ = C₂H₅<br>R₃ = NH₂<br>X = O | (IIIL) | R = CH₃<br>R₂ = H<br>R₃ = N(CH₃)₂<br>X = S |

-continued (IIIC)  R = CH₃
        R₂ = CH₃
        R₃ = NH₂
        X = NH (IIIH)  R = CH₃
        R₂ = H
        R₃ = NHCH₃
        X = O (IIIM)  R = CH₂CH₂OH
        R₂ = H
        R₃ = NH₂
        X = S (IIID)  R = CH₃
        R₂ = H
        R₃ = NHCH₃
        X = NH (III I) R = CH₂CH₂OH
        R₂ = H
        R₃ = NH₂
        X = O (IIIN)  R = CH₂CH₃
        R₂ = H
        R₃ = NH₂
        X = S (IIIE)  R = CH₂CH₂OH
        R₂ = H
        R₃ = NH₂
        X = NH (IIIJ)  R = CH₃
        R₂ = H
        R₃ = NH₂
        X = S (IIIO)  R = CH₃
        R₂ = H
        R₃ = C₂H₅
        X = O (IIIP)  R = CH₂CH₂OH
        R₂ = H
        R₃ = CH₃
        X = O (IVA)  R = CH₃       (IVB)  R = CH₃       (IVC)  R = C₂H₅      (VA)  R₂ = H
       R₁ = C₂H₅            R₁ = CH₃             R₁ = CH₃            X = S
       R₂ = H                R₂ = H               R₂ = H              R₃ = NH₂
       X = S                 X = S                X = S
       R₃ = NH₂              R₃ = NH₂             R₃ = NHCH₃

(VB)  R₂ = H
      X = S
      R₃ = N(CH₃)₂

III, IV or V
Δ

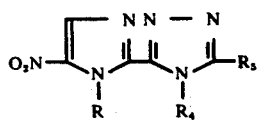

VI (VIA)  R = CH₃        (VID)  R = CH₃
       R₄ = H                R₄ = CH₃
       R₅ = CH₃              R₅ = NH₂

(VIB)  R = CH₃        (VIE)  R = CH₂CH₂OH
       R₄ = H                R₄ = H
       R₅ = NH₂              R₅ = NH₂

(VIC)  R = CH₃        (VIF)  R = CH₃
       R₄ = H                R₄ = H
       R₅ = NHCH₃            R₅ = OH (VIG)  R = CH₃
       R₄ = CH₃
       R₅ = OH (VIH)  R = CH₂CH₂OH
       R₄ = H
       R₅ = OH (VI I) R = CH₃
       R₄ = H
       R₅ = C₂H₅

(VIJ)  R = CH₂CH₂OH
       R₄ = H
       R₅ = CH₃

III, IV or V

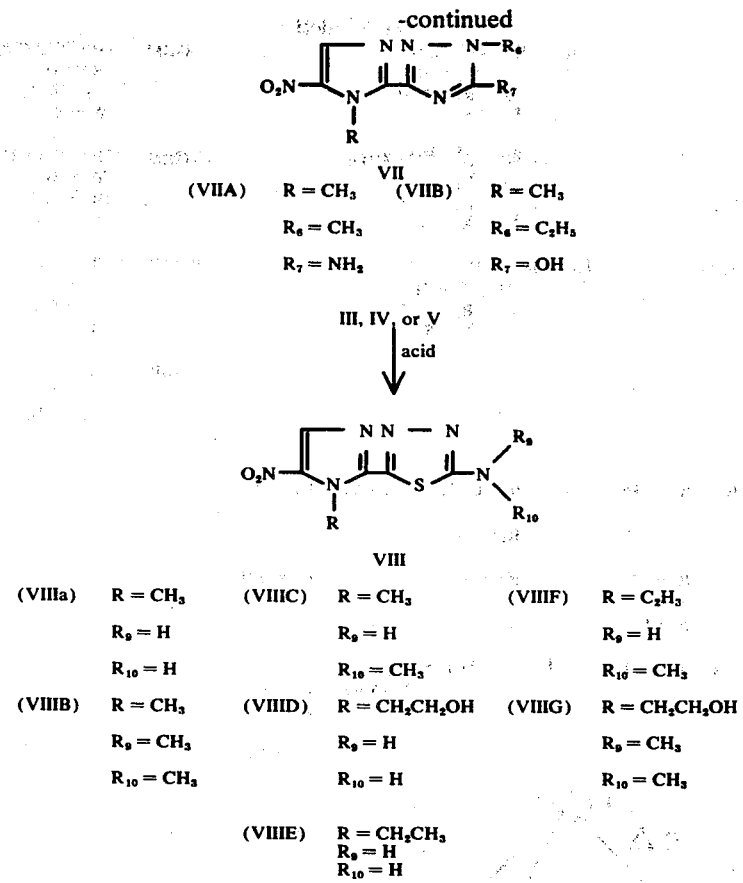

wherein $R_1$ is lower alkyl and R, $R_2$, $R_3$, $R_4$, $R_5$, $R_6$, $R_7$, $R_8$, $R_9$, $R_{10}$, X and Y are as hereinbefore described.

Also, in accordance with the invention a 1-loweralkylsubstituted-5-nitro-2-imidazolecarboxylic acid is treated with oxalyl chloride to give the 1-loweralkyl-5-nitro-2-imidazolecarboxylic acid chloride which is converted to the corresponding 2-imidazolecarbonyl semicarbazide or thiosemicarbazide by reaction with semicarbazide or thiosemicarbazide in an organic solvent. When the thus prepared semicarbazide or thiosemicarbazide has $R_2 = H$ (see below), it can then be cyclized to the oxadiazolyl or thiadiazolyl imidazoles by treatment thereof, in the case of the thiosemicarbazide, with a strong mineral acid at an elevated temperature preferably between about 50° C. and 100° C. and, in the case of the semicarbazide, with a condensing agent such as phosphorus oxychloride or thionylchloride. The oxadiazolyl or thiadiazolyl imidazole is then readily recovered from the reaction mixture by treatment of the mixture with water, followed by filtration.

The reactions are illustrated graphically below:

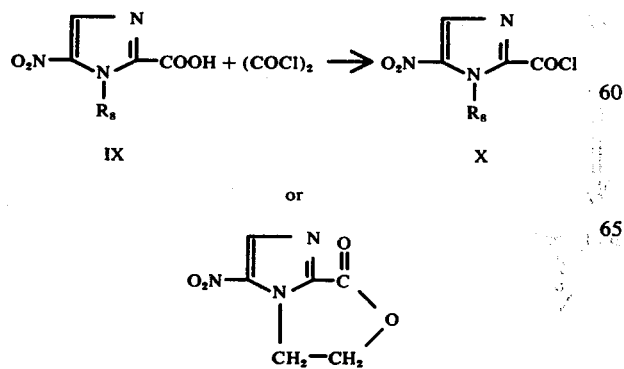

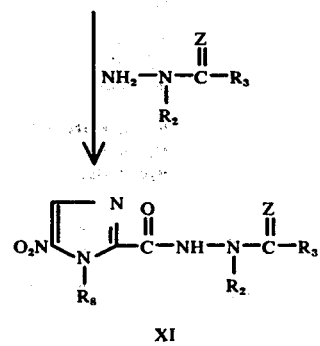

-continued (XIA) $R_8 = CH_3$
$R_2 = H$
$R_3 = NH_2$
$Z = S$ (XIB) $R_8 = CH_3$
$R_2 = H$
$R_3 = NH\ i\text{-}C_3H_7$
$Z = S$ (XIC) $R_8 = CH_3$
$R_2 = CH_3$
$R_3 = NHC_2H_5$
$Z = S$ (XID) $R_8 = CH_3$
$R_2 = H$
$R_3 = NH_2$
$Z = NH$ (XIE) $R_8 = CH_3$
$R_2 = H$
$R_3 = NH_2$
$Z = O$ $\Delta$ and acid or condensing agent (XIF) $R_8 = CH_3$
$R_2 = H$
$R_3 = NHCH_3$
$Z = O$ (XIG) $R_8 = CH_2CH_2OH$
$R_2 = H$
$R_3 = NH_2$
$Z = S$

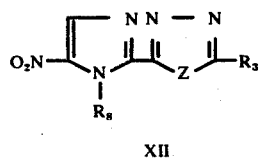

XII (XIIA) $R_8 = CH_3$
$R_3 = NH_2$
$Z = O$ (XIIB) $R_8 = CH_3$
$R_3 = NHCH_3$
$Z = O$ (XIIC) $R_8 = CH_3$
$R_3 = NH_2$
$Z = S$ wherein Z is oxygen or sulfur and $R_2$, $R_3$, and $R_8$ are as hereinbefore described.

The process of the present invention is highly effective for the preparation of compounds useful for the control of bacterial, parasitic and protozoal infections in poultry and animals.

The novel compounds of the invention find utility as antimicrobial agents effective against Trichomonas vaginalis and Salmonella gallinarum infections in poultry and animals and also show a substantial amount of seedicidal activity in the plant science area. For the treatment of animals and poultry generally about .025% to 0.1% by weight of the active compound will be throughly admixed with the food and administered as such to said animals or poulty. If desired, however, the compounds may be prepared as liquids for use in drinking water or as an oral drench, in which case the active compound is dissolved or suspended in a nontoxic pharmaceutically acceptable carrier and administered in an amount sufficient to produce generally about 100 to 1,000 mg./kg., and preferably 100 to 500 mg./kg. of body weight of active material to the animal under treatment.

DETAILED DESCRIPTION

The following examples describe in detail the preparation of representative compounds of this invention and their use in treating fowl typhoid, enteritis and colibacillosis.

EXAMPLE 1

Preparation of
2-(1-Methyl-5-nitro-2-imidazolecarboximidoyl)-1-acetylhydrazine (IIIA)

In 200 ml. of methanol, 12 g. (0.06 mole) of ethyl 1-methyl-5-nitro-2-imidazolecarboxumidate and 4.9 g. (0.066 mole) of acetyl hydrazine are refluxed for 30 hours. The yellow compound is collected, washed with cold methanol and dried to give 12.97 g. of the title compound, melting point 194° C.

Similarly, 2-propionylhydrazine is reacted with ethyl-1-methyl-5-nitro-2-imidazolecarboximidate to afford 2-(1-methyl-5-nitro-2-imidazolecarboximidoyl)-1-propionylhydrazine (IIIO). 5-nitro-2-imidazolecarboximidoyl) -1-propionylhydrazine (IIIO).

In the above manner, 2-(1-(2-hydroxyethyl)-5-nitro-2-imidazolecarboximidoyl)-1-acetylhydrazine (IIIP), is prepared by reacting acetyl hydrazine with the cyclic iminoester of the formula

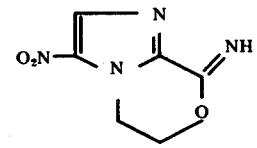

The cyclic iminoester is prepared by reacting 2-cyano-1-(2-hydroxyethyl)-5-nitroimidazole in inert solvent with alkali metal alkoxide.

EXAMPLE 2

Preparation of
2-(5-Methyl-4H-1,2,4-triazol-3-yl)-1-methyl-5-nitromidazole (VIA)

In 100 ml. of glacial acetic acid 6.2 g. (0.0274 mole) of 2-(1-methyl-5-nitro-2-imidazolecarboximidoyl)-1-acetylhydrazine is refluxed for 4 ½ hours. The mixture is cooled, diluted with water to give 5.33 g. of the above compound, melting point 329°–333°(dec).

In the same manner 2-(5-ethyl-4H-1,2,4-triazol-3-yl)-1-methyl-5-nitroimidazole (VI I) is prepared from 2-(1-methyl-5-nitro-2-imidazolecarboximidoyl)-1-propionylhydrazine.

Using the above procedure 2-(5-methyl-4H-1,2,4-triazol-3-yl)-1-(2-hydroxyethyl)-5-nitroimidazole (VI J) is prepared from 2-[1-(2-hydroxyethyl)-5-nitro-2-imidazolecarboximidoyl]-1-acetylhydrazine.

EXAMPLE 3

Preparation of
2-(1-Methyl-5-nitro-2-imidazolecarboximidoly)-1-amidino hydrazine hydrochloride (IIIB)

In 10 ml. of ethanol, 8.2 g. (0.06 mole) of aminoguanidine bicarbonate is treated with saturated ethanolic hydrogen chloride until carbon dioxide is no longer evolved. The mixture is evaporated to dryness, 90 ml. of dry dimethylforamide and 11.9 g. (0.06 mole) of ethyl-1-methyl-5-nitro-2-imidazolecarboximidate are added to give a yellow slurry which is heated at 65°–70° C for 1½ hours with stirring. The mixture is cooled, 160 ml. of ether added, and the above compound collected, melting point 273°–274° C (dec.); the yield is 12.6 g. (80%).

Similarly, 2-(1-methyl-5-nitro-2-imidazolecarboximidoyl)-1-amidino-1-methylhydrazine hydrochloride (IIIC) and 2-(1-methyl-5-nitro-2-imidazolecarboximidoyl)-1-methylamidinohydrazine hydrochloride (IIID) are prepared by reacting ethyl-1-methyl-5-nitro-2-imidazolecarboximidate with 1-amino-1-methylguanidine hydrochloride and 1-amino-3-methylguanidine hydrochloride, respectively. In the like manner, 2-[1-(2-hydroxyethyl)-5-nitro-2-imidazolecarboximidoyl]-1-amidinohydrazine hydrochloride (IIIE) is prepared by reacting aminoguanidine hydrochloride with the cyclic imino ester described in Example 1.

EXAMPLE 4

Preparation of 2-(5-Amino-4H-1,2,4-triazol-3-yl)-1-methyl-5-nitroimidazole (VIB)

In 110 ml. of nitrobenzene, 7.6 g. (0.029 mole) of 2-(1-methyl-5-nitro-2-imidazolecarboximidoyl)-1-amidinohydrazine hydrocloride is stirred at reflux temperature for 2 ¾ hours, cooled, and the solid collected. This solid is washed with ethyl alcohol, ether, and air-dried to give 6 g. of the title compound, melting point 278°–280° (dec). The product is purified by removing soluble impurities in a Soxhlet extractor with 95% ethanol. The insoluble products melts at 297°–299° (dec).

In the same manner, a mixture of 2-(4H-5-methylamino-1,2,4-triazol-3-yl)-1-methyl-5-nitroimidazole (VIC) and 2-(5-amino-4-methyl-1,2,4-triazol-3-yl)-1-methyl-5-nitroimidazole (VID) are prepared from 2-(1-methyl-5-nitro-2-imidazolecarboximidoyl)-1-methylamidinohydrazine hydrochloride, and 2-(5-amino-1-methyl-1,2,4-triazol-3-yl)-1-methyl-5-nitroimidazole (VIIA) is prepared from 2-(1-methyl-5-nitro-2-imidazolecarbocimidoyl)-1-amidino-1-methylhydrazine hydrochloride.

Similarly, 2-(5-amino-4H-1,2,4-triazol-3-yl)-1-(2-hydroxyethyl)-5-nitroimidazole (VIE) is prepared from 2-[1-(2-hydroxyethyl)-5-nitro-2-imidazolecarboximidoyl]-1-amidinohydrazine hydrochloride.

EXAMPLE 5

Preparation of 1-(1'-Methyl-5-nitro-2-imidazolecarboximidoyl)-semicarbazide (IIIF)

The above compound is prepared by stirring a powdered mixture of 19.8 g. (0.1 mole) of ethyl 1-methyl-5-nitro-2-imidazolecarboximidate and 11.2 g. (0.1 mole) of semicarbazide hydrochloride in 200 ml. of 50% aqueous ethanol. The yellow product is collected after 90 minutes and washed with water, methanol, and ether, respectively, melting point above 300° C; the yield is 10 g. (44%).

The addition of 0.122 mole of sodium acetate to the mixture improved the yield to 86%.

In a similar manner, 2-ethylsemicarbazide and 4-methylsemicarbazide are reacted with ethyl 1-methyl-5-nitro-2imidazolecarboximidate to give 1-(1-methyl-5-nitro-2-imidazolecarboximidoyl)-2-ethylsemicarbazide (IIIG) and 1-(1-methyl-5-nitro-2-imidazolecarboximidoyl)-4-methylsemicarbazide (IIIH), respectively.

Similarly, 1-[1-(2-hydroxyethyl)-5-nitro-2-imidazolecarboximidoyl]semicarbazide (III I) is prepared by reacting semicarbazide hydrochloride with the previously mentioned cyclic iminoester of Example 1.

EXAMPLE 6

Preparation of 1-(1-Methyl-5-nitro-2-imidazolecarboximidoyl)-3-thiosemicarbazide (IIIJ)

A mixture of 1.0 g. of ethyl 1-methyl-5-nitro-2-imidazolecarboximidate and 0.46 g. of thiosemicarbazide in 20 ml. of glacial acetic acid is heated at reflux for 45 minutes. Water is added and the yellow solid is filtered, washed with water and dried affording the amidine, melting point 210°–212° C., dec.

When the above procedure is carried out using 4-methyl-3-thiosemicarbazide and 4,4-dimethyl-3-thiosemicarbazide, 4-methyl-1-(1-methyl-5-nitro-2'-imidazolecarboximidoyl)-3-thiosemicarbazide (IIIK) and 4,4-dimethyl-1-(1-methyl-5-nitro-2-imidazolecarboximidoyl)-3-thiosemicarbazide (IIIL) are obtained.

In a similar manner, 1-[1-(2-hydroxyethyl)-5-nitro-2-imidazolecarboximodoyl]-3-thiosemicarbazide (IIIM) is obtained by treating 1-(2-hydroxyethyl)-5-nitro-2-imidazolecarboximidic acid, delta-lactone, with thiosemicarbazide.

According to the above procedure, ethyl 1-ethyl-5-nitro-2-imidazolecarboximidate and thiosemicarbazide are allowed to react to give 1-(1-ethyl-5-nitro-2-imidazolecarboximidoyl)-3-thiosemicarbazide (IIIN).

EXAMPLE 7

Preparation of 1-(1-Methyl-5-nitro-2-imidazolecarbonyl)-3-thiosemicarbazide (XIA)

To 5 ml. of oxalyl chloride, stirred in ice bath, is added 1.0 of 1-methyl-5-nitro-2-imidazolecarboxylic acid, in portions. The resulting suspension is stirred at room temperature overnight. Benzene is added, the mixture is filtered and the filtrate is evaporated to dryness. The residue, 1-methyl-5-nitro-2-imidazolecarboxylic acid chloride, is sufficiently pure to use in subsequent reactions To 1-methyl-5-nitro-2-imidazolecarboxylic acid chloride (1.1 g.) in 25 ml. of dry tetrahydrofuran is added 0.55 g. powdered thiosemicarbazide and the mixture is stirred at room temperature for 24 hours. The reaction mixture is evaporated to dryness and water is added. The solution is made basic with sodium hydroxide and the solid is filtered, washed with water and dried affording 1-(1-methyl-5-nitro-2-imidazolecarbonyl)-3-thiosemicarbazide.

When the above procedure is followed using 4-isopropyl-3-thiosemicarbazide and 4-ethyl-2-methyl-3-thiosemicarbazide, 1-(1-methyl-5-nitro-2-imidazolecarbonyl)-4-isopropyl-3-thiosemicarbazide (XIB) and 4-ethyl-2-methyl-1-(1-methyl-5-nitro-2-imidazolecarbonyl)-3-thiosemicarbazide (XIC), respectively, are obtained.

In a similar manner, 2-(1-methyl-5-nitro-2-imidazolecarbonyl)-1-amidinohydrazine (XID), 1-(1-methyl-5-nitro-2-imidazolecarbonyl)semicarbazide (XIE), and 1-(1-methyl-5-nitro-2-imidazolecarbonyl)-4-methyl semicarbazide (XIE), are obtained from the reaction of 1-methyl-5-nitro-2-imidazolecarboxylic acid chloride with aminoguanidine bicarbonate, semicarbazide and 4-methylsemicarbazide, respectively.

EXAMPLE 8

Preparation of 1-[1-(2-Hydroxyethyl)-5-nitro-2-imidazolecarbonyl]-3-thiosemicarbazide (XIG)

A mixture of 1-(2-hydroxyethyl)-5-nitroimidazole-2-carboxylic acid delta-lactone (1.83 g) and thiosemicarbazide (0.91 g) in 50 ml. of tetrahydrofuran is heated at reflux for three hours. The solvent is evaporated and the residue is slurried with water and the solid is filtered, washed with water and dried giving 1-[1-(2-hydroxyethyl)-5-nitro-2-imidazolecarbonyl]-3-thiosemicarbazide.

EXAMPLE 9

Preparation of 2-(2-Amino-1,3,4-thiadiazol-5-yl)-1-methyl-5-nitroimidazole (VIIIA or XIIC)

To 0.05 g. of 1-(1-methyl-5-nitro-2-imidazolecarbonyl)-3-thiosemicarbazide is added 0.5 ml. of conc. sulfuric acid and the mixture is heated on a steam bath for 30 minutes. Ice is added to the reaction mixture and the solid is filtered. The filtrate is made basic with sodium hydroxide and cooled in an ice bath. The solid is filtered, washed with water and dried affording 17 mg. (37%) of 2(2-amino-1,3,4-thiodiazol-5-yl)-1-methyl-5-nitroimidazole.

EXAMPLE 10

Preparation of 2-(2-Amino-1,3,4-thiadiazol-5-yl)-1-methyl-5-nitroimidazole (VIIIA)

1-(1-Methyl-5-nitro-2-imidazolecarboximidoyl)-3-thiosemicarbazide (0.3 g.) is heated with 7 ml. of 6N hydrochloric acid for 15 minutes. The resulting solution is cooled and diluted with water. The solid is filtered, washed with water and dried affording 2-(2-amino-1,3,4-thiadiazol-5-yl)-1-methyl-5-nitroimidazole, melting point 266°–8°.

In a similar manner, 4,4-dimethyl-1-(1methyl-5-nitro-2-imidazolecarboximidoyl)-3-thiosemicarbazide, 4-methyl-1-(1-methyl-5-nitro-2-imidazolecarboximidoyl)-3-thiosemicarbazide and 1-(1-[2-hydroxyethyl]-5-nitro-2-imidazolcarboximidoyl)-3-thiosemicarbazide yield respectively, 2-(2-dimethylamino-1,3,4-thiadiazol-5-yl)-1-methyl-5-nitroimidazole (VIIIE), 2-(2-methylamino-1,3,4-thiadiazol-5-yl)-1-methyl-5-nitroimidazole (VIIIC) and 2-(2-amino-1,3,4-thiadiazol-5-yl)-1-(2-hydroxyethyl)-5-nitroimidazole (VIIID). According to the above procedure, 2-(2-amino-1,3,4-thiadiazol-5-yl)-1-ethyl-5-nitroimidazole (VIIIE) is obtained from 1-(b 1-ethyl-5-nitro-2-imidazolecarboximidoyl)-3-thiosemicarbazide.

EXAMPLE 11

Preparation of 2(2-Amino-1,3,4-oxadiazol-5-yl)-1-methyl-5-nitroimidazole (XIIA)

1-(1-Methyl-5-nitro-2-imidazolecarbonyl)semicarbazide (5 g.) is heated under reflux in 50 ml. of phosphorous oxychloride for 1 hour. The reaction mixture is added slowly to water maintained at 15° C. by occasional additions of ice. The aqueous mixture is brought to pH 7 with potassium carbonate and the solid 2-(2-amino-1,3,4-oxadiazol-5yl)-1-methyl-5-nitroimidazole filtered off, washed with water, and dried.

In similar fashion, 2-(2-methylamino-1,3,4-oxadiazol-5-yl)-1-methyl-5-nitroimidazole (XIIB) is prepared from 1-(1-methyl-5-nitro-2-imidazolecarbonyl)-4-methylsemicarbazide.

EXAMPLE 12

Preparation of 1-Methyl-5-nitro-2-[5-oxo-(Δ²-1,2,4-triazolin-3-yl)-imidazole (VIF)

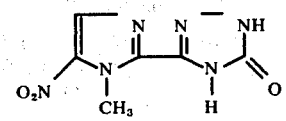

In 50 ml of dimethylformamide, 7.8 g. of 1-(1-methyl-5-nitro-2-imidazolecarboximidoyl)semicarbazide is stirred at 140°–150° C. until the yellow solid darkens, dissolves to give a dark-brown solution, and begins to deposite grey crystals. The mixture is cooled, diluted with 125 ml. of ethyl alcohol, poured onto ice, and the solid collected. This solid is washed with hot dimethylformamide to give the light-brown title compound, melting point >320°.

Similarly, 1-methyl-5-nitro-2-[1-ethyl-5-oxo(Δ²-1,2,4-triazolin-3-yl)imidazole (VIIB) and 1-methyl-5-nitro-2-[4-methyl-5-oxo-(Δ²-1,2,4-triazolin-3:yl)-]imidazole (VIG) are prepared from 1-(1-methyl-5-nitro-2-imidazolecarboximidoyl 1)-2-ethyl-semicarbazide and 1-(1-methyl-5-nitro-2-imidazolecarboximidoyl)-4-methylsemcarbazide, respectively.

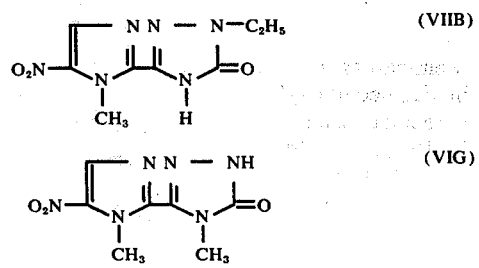

Similarly, 1-(2-hydroxyethyl)-5-nitro-2-[5-oxo-(Δ²-1,2,4-triazolin-3-yl)]imidazole (VIH) is prepared from 1-[1-(2-hydroxyethyl)-5-nitro-2-imidazolecarboximidoyl]semicarbazide.

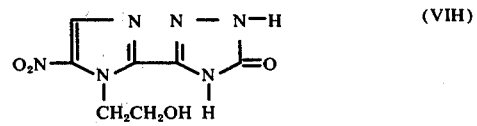

EXAMPLE 13

Preparation of 1-(1-Methyl-5-nitro-2-imidazolecarboximidoyl)-3-thiosemicarbazide (IIIJ)

To a stirred solution of ethyl 1-methyl-5-nitro-2-imidazolecarboximidate (0.198 g., 0.001 mole) in 10 ml. of absolute ethanol is added thiosemicarbazide (0.091 g., 0.001 mole) and 1 ml. of glacial acetic acid. The mixture is heated at reflux for 1¼ hours and is cooled in an ice bath. The orange-red solid is filtered washed and dried affording 0.173 g. of the title compound, melting point 210°–214°, dec.

When an equimolar amount of methyl 1-methyl-5-nitro-2-imidazolecarboximidate is substituted for the ethyl carboximidate in this procedure and the reaction mixture stirred at room temperature for 3 hours, the compound (IIIJ) is also obtained in good yield.

EXAMPLE 14

Preparation of 1-(1-Methyl-5-nitro-imidazolecarboximidoyl)-3-thiosemicarbazide (IIIJ)

To a stirred mixture of ethyl 1-methyl-5-nitro-2-imidazolecarboximidate (0.198 g., 0.001 mole) and thiosemicarbazide (0.091 g., 0.001 mole) in 5 ml. of methanol is added 1 drop of conc. $H_2SO_4$ and the mixture is stirred at room temperature for 50 minutes. The solid is filtered and washed with methanol, yielding 0.149 g. of the title compound, melting point 200°–201° C. dec.

EXAMPLE 15

Preparation of Ethyl 1-methyl-5-nitro-2-imidazolecarboxylate thiosemicarbazone (IVA) and 1-(1-methyl-5-nitro-2-imidazolecarboximidoyl)-3-thiosemicarbazide To a mixture of ethyl 1-methyl-5-nitro-2-imidazolecarboximidate (1.98 g., 0.01 mole) and thiosemicarbazide (0.91 g., 0.01 mole) in 50 ml. of absolute ethanol is added 5.37 N ethanolic HCl (1.86 ml., 0.01 mole). The mixture is stirred at room temperature for 3½ hours. The yellow solid is filtered, washed with ethanol and dried, giving 1.27 g. of a mixture of 1-(1-methyl-5-nitro-2-imidazolecarboximidoyl)-3-thiosemicarbazide and ethyl 1-methyl-5-nitro-2-imidazolecarboxylate thiosemicarbazone. The mixture is recrystallized from dry dimethylsulfoxide, affording 0.315 g. of ethyl 1-methyl-5-nitro-2-imidazole-carboxylate thiosemicarbazone, melting point 202°–204° dec. Both infrared and nuclear magnetic resonance spectra show the presence of an ethoxyl group in this product.

When the above procedure is carried out using 4-methyl-3-thiosemicarbazide and 4,4-dimethyl-3-thiosemicarbazide, the 4-methyl-3-thiosemicarbazone of ethyl 1-methyl-5-nitro-2-imidazolecarboxylate and the 4,4-dimethyl-3-thiosemicarbazone of ethyl 1-methyl-5-nitro-2-imidazolecarboxylate, respectively, are obtained.

Use of methyl 1-methyl-5-nitro-2-imidazolecarboximidate in place of ethyl 1-methyl-5-nitro-2-imidazolecarboximidate in the above reactions gives the corresponding thiosemicarbazone of methyl 1-methyl-5-nitro-2-imidazolecarboxylate. Similarly, use of 1-(2-hydroxyethyl)-5-nitro-2-imidazolecarboximidic acid, delta-lactone, gives the thiosemicarbazone of 1-(2-hydroxyethyl)-5-nitro-2-imidazolecarboxylic acid, delta-lactone.

EXAMPLE 16

Preparation of 2(2-amino-1,3,4-thiadiazol-5yl)-1-methyl-5-nitroimidazole

To a stirred mixture of ethyl 1-methyl-5-nitro-2-imidazolecarboxylate thiosemicarbazone (0.050 g., of 0.0018 mole) and 10 ml. of absolute ethanol is added 0.3 ml. of 5.37 N ethanolic HCl. The mixture is heated at reflux for hours and is diluted with water. The solution is made alkaline with conc. ammonium hydroxide and the ethanol is evaporated. The yellow solid is filtered, washed with water and dried, yielding 0.013 g. of the above compound.

In a similar manner, acid treatment of the mixture of 1-(1-methyl-5-nitro-2-imidazolecarboximidoyl)-3-thiosemicarbazide and ethyl 1-methyl-5-nitro-2-imidazolecarboxylate thiosemicarbazone, gives the title compound.

The same procedure used with methyl 1-methyl-5-nitro-2-imidazolecarboxylate thiosemicarbazone gives the above compound. With ethyl 1-methyl-5-nitro-2-imidazolecarboxylate, 4-methyl-3-thiosemicarbazone and with ethyl 1-methyl-5-nitro-2-imidazolecarboxylate, 4,4-dimethyl-3-thiosemicarbazone, there is obtained, respectively, 2-methylamino-5-(1-methyl-5-nitro-2-imidazolyl)-1,3,4-thiadiazole and 2-dimethylamino-5-(1-methyl-5-nitro-2-imidazolyl)-1,3,4-thiadiazole.

EXAMPLE 17

Preparation of 2-(2-Amino-1,3,4-thiadiazol-5-yl)-1-methyl-5-nitroimidazole 1-(1-Methyl-5-nitro-2-imidazolecarboximidoyl)-3-thiosemicarbazide is cyclized as in Example 10 with the exception that the 0.3 g. of the thiosemicarbazide in 7 ml. of 6N hydrochloric acid is replaced by 0.49 g. of the thiosemicarbazide in 5 ml. of methanol plus 0.5 ml. of concentrated hydrochloric acid. The cyclization is also effected by the use of 0.49 g. of the thiosemicarbazide in 5 ml. of methanol plus 0.5 ml. of 6N ethanolic hydrogen chloride. In each of these variations, a 78% yield of the title compound is realized. The cyclization is likewise accomplished by the use of dilute aqueous sulfuric acid, phosphoric, nitric, p-toluenesulfonic, benzene sulfonic, methylsulfonic or hydrobromic acid.

EXAMPLE 18

Utilization of compounds of the present invention in controlling fowl typhoid

The effectiveness of the compounds of the invention or products prepared from the intermediate compounds therein disclosed for controlling fowl typhoid is demonstrated by the following tests.

One day old sex-linked pullet chicks are infected orally by gavage with 0.5 ml. of a $10^{-2}$ dilution of a five-hour Trypticase Soy Broth culture of *Salmonella gallinarum*, the causative agent of fowl typhoid. Each chick receive approximately 6 × $10^5$ viable cells.

Medication is administered continuously in the feed, beginning 3 hours before infection and continuing for 10 days, at which time the test is terminated and the number of survivors in each group recorded. The results are compared with two control groups of chicks, the first group comprising 20 chicks which are infected and untreated, and the second group comprising 10 chicks which are infected and untreated. The results of the test are set forth in the following table:

TABLE I

| Compound | Dose* | Total Checks Tested | Survivors |
|---|---|---|---|
| 2-(2-Amino-1,3,4-thiadiazol-5-yl)-1-methyl-5-nitroimidazole | 0.1% | 10 | 9 |
| | 0.05% | 5 | 5 |
| | 0.025% | 5 | 5 |
| | 0.006% | 5 | 1 |
| 2-(2-Methylamino-1,3,4-thiadiazol-5-yl)-1-methyl-5-nitroimidazole | 0.1% | 5 | 3 |

TABLE I-continued

| Compound | Dose* | Total Checks Tested | Survivors |
|---|---|---|---|
| 2-(2-Dimethylamino-1,3,4-thiadiazol-5-yl)-1-methyl-5-nitroimidazole | 0.1% | 5 | 4 |
| 2-(1-Methyl-5-nitro-2-imidazolecarboximidoyl)-1-acetylhydrazine | 0.1% 0.025% | 5 5 | 4 |
| 2-(2-Amino-5-oxadiazolyl)-1-methyl-5-nitroimidazole | 0.1% 0.025% | 10 10 | 10 10 |
| 2-(2-Methylamino-5-oxadiazolyl)-1-methyl-5-nitroimidazole | 0.1% 0.025% | 10 10 | 10 10 |
| Control | | | |
| Infected - Untreated | | 20 | 0 |
| Uninfected - Untreated | | 10 | 10 |

*Dose is in terms of percentage by weight of the feed.

EXAMPLE 19

Utilization of a compound of the present invention in controlling enteritis

This example demonstrates the effectiveness of 2-(2-amino-1,3,4-thiadiazol-5-yl)-1-methyl-5-nitroimidazole in controlling enteritis. Three groups of ten female Swiss Webster mice weighing 20 gm. are infected intraperitoneally with 0.5 ml. of $10^{-2}$ dilution of a five-hour Trypticase Soy Broth culture of *Salmonella choleraesuis* var. kunzendorf, the causative agent of enteritis in pigs, an organism originally recovered from a field outbreak of *Salmonella choleraesuis* var. kunzendorf in pigs. Each mouse receives approximately $4.6 \times 10^7$ cells as the inoculating dose.

The mice are fed a medicated feed, which is a commercial mouse chow containing the compound 2-(2-amino-1,3,4-thiadiazole-5-yl)-1-methyl-5-nitroimidazole, for 3 hours before infection until 7 days after infection. The mice are held for an additional 7 days after the medication is stopped, and the number of survivors in each group recorded. The medicated feed is prepared by thoroughly admixing calculated amounts of 2-(2-amino-1,3,4-thiadiazol-5-yl)-1-methyl-5-nitroimidazole with commercial mouse chow to provide essentially uniform distribution in the feed offered. The above results are compared with two control groups of ten mice each, in which one control group is infected and untreated, and the second control group is uninfected and untreated. The results of the test are set forth in the following table:

TABLE II

| Compound | Dose* | Total Mice Tested | Survivors |
|---|---|---|---|
| 2-(2-amino-1,3,4-thiadiazol-5-yl)-1-methyl-5-nitroimidazole | 0.1% 0.025% 0.006% | 10 10 10 | 10 9 1 |
| Control | | | |
| Infected - Untreated | | 10 | 2 |
| Uninfected - Untreated | | 10 | 10 |

*Dose is in terms of percentage by weight of commercial mouse chow

EXAMPLE 20

Utilization of compounds of the present invention in controlling colibacillosis

This example demonstrates the effectiveness of 2-(2-amino-1,3,4-thiadiazol-5-yl)-1-methyl-5-nitroimidazole in controlling colibacillosis in poultry.

Three groups of 10 five-day old sex-linked pullet chicks are infected parenterally, in the left thoracic air sac, with 0.2 ml. of a $10^{-1}$ dilution of a Trypticase Soy Broth culture of *Escherichia coli*, the causative agent of colibacillosis in poultry. The compound 2-(2-amino-1,3,4-thiacoliazol-5-yl)-1-methyl-5-nitroimidazole is administered by gavage as a single oral dose in an aqueous solution or suspension, and the chicks are permitted to feed ad libitum. A nutritionally balanced diet is employed. Twelve days after treatment, the test is terminated and the number of survivors in each group recorded. The results are compared with two control groups of 20 chicks each, in which one control group is infected and untreated, and the second control group is uninfected and untreated. The results of the test are set forth in the following table:

TABLE III

| Compound | Dose* | Total Chicks Tested | survivors |
|---|---|---|---|
| 2-(2-amino-1,3,4-thiadiazol-5-yl)-1-methyl-5-nitroimidazole | 160 mg. 80 " 40 " | 10 10 10 | 10 10 10 |
| Control | | | |
| Infected - Untreated | | 20 | 2 |
| Uninfected - Untreated | | 20 | 20 |

*Dose is in terms of milligrams per kilogram of body weight.

EXAMPLE 21

Control of Trichomonas vaginalis Infections

The activity of the compounds of the present invention for controlling *Trichomonas vaginalis* infections is demonstrated in the following example wherein mice are inoculated with 50,000 culture-derived *Trichomonas vaginalis* (Thoms strain) and then treated with test compounds to determine whether such compound is active for controlling the above named disease organism. In these tests 100, 200 or 1,000 mg./kg. of body weight of test compound is administered in a single oral dose by gavage one day after inoculation. Six days after inoculation, scrapings from the subcutaneous sites of inoculation are searched microscopically for motile trichomonads and antitrichomonal activity is concluded in those instances where motile trichomonads are eliminated from lesions present at the site of inoculation.

In these tests all mice received a standard commercial mouse chow and water provided ad libitum throughout the test period. The data obtained are provided in table form below.

TABLE IV

| Compound | Dose mg./kg. | Total Mice Infected | Cleared | Percentage cleared |
|---|---|---|---|---|
| 2-(5-methyl-4H-1,2,4-triazol-3-yl)-1-methyl-5-nitroimidazole | 200 | 5 | 5 | 100 |
| 2-(5-amino-4H-1,2,4-triazol-3-yl)-1-methyl-5-nitroimidazole | 1000 | 5 | 5 | 100 |

TABLE IV-continued

| Compound | Dose mg./kg. | Total Mice Infected | Cleared | Percentage cleared |
|---|---|---|---|---|
| 1-(1-methyl-5-nitro-2-imidazolecarboximidoyl)semicarbazide | 100 | 5 | 2 | 40 |

We claim:

1. A compound selected from the group consisting of the formulae:

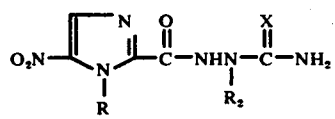

and

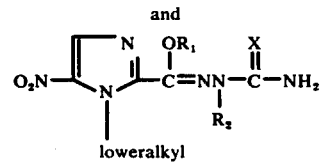

loweralkyl wherein R is loweralkyl or hydroxyloweralkyl; $R_1$ is loweralkyl; and X is sulfur or oxygen.

2. A compound according to claim 1 having the structure:

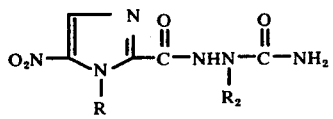

wherein R and $R_2$ are as described in claim 1.

3. The compound according to claim 1, 1-(1-methyl-5-nitro-2-imidazolecarbonyl)semicarbazide.

4. The compound according to claim 1, 1-(1-methyl-5-nitro-2-imidazolecarbonyl)-3-thiosemicarbazide.

5. The compound according to claim 1, methyl-1-methyl-5-nitro-2-imidazolecarboxylate thiosemicarbazone.

* * * * *